(12) United States Patent
Hsieh

(10) Patent No.: US 6,226,350 B1
(45) Date of Patent: May 1, 2001

(54) METHODS AND APPARATUS FOR CARDIAC SCORING WITH A MULTI-BEAM SCANNER

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/261,778

(22) Filed: Mar. 3, 1999

Related U.S. Application Data

(60) Provisional application No. 60/114,336, filed on Dec. 31, 1998.

(51) Int. Cl.[7] .................................................. H05G 1/00

(52) U.S. Cl. ...................... 378/98; 378/98.2; 378/98.11

(58) Field of Search .................. 378/98, 98.2, 98.11, 378/98.12

(56) References Cited

U.S. PATENT DOCUMENTS

| | | | |
|---|---|---|---|
| 4,720,843 | * | 1/1988 | Haaker et al. .................. 378/98.12 |
| 5,930,329 | * | 7/1999 | Navab .............................. 378/98.12 |
| 6,005,917 | * | 12/1999 | Andersson et al. ............. 378/98.12 |

* cited by examiner

Primary Examiner—David V. Bruce
(74) Attorney, Agent, or Firm—Armstrong Teasdale LLP; Christian G. Cabou

(57) ABSTRACT

The present invention, in one form, includes an imaging system having a x-ray source and detector array and a reconstruction algorithm. The algorithm removes overlapping structures from a patient scan so that enhanced images representing a moving heart are generated. More specifically and in one embodiment, an estimated background representing the overlapping structures is determined using the projection data. The estimated background is then subtracted from the projection data to generate filtered data. The filtered data is then used to generate an enhanced image so that cardiac calcification may be identified.

31 Claims, 2 Drawing Sheets

METHODS AND APPARATUS FOR CARDIAC SCORING WITH A MULTI-BEAM SCANNER

CROSS REFERENCE TO RELATED APPLICATION

This application claims the benefit of U.S. Provisional Application No. 60/114,336, filed Dec. 31, 1998.

BACKGROUND OF THE INVENTION

This invention relates generally to an imaging system, and more particularly, to a reconstruction algorithm for generating images representing a moving heart.

In at least one known imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In at least one known type of imaging system, commonly known as a computed tomography (CT) system, a group of x-ray attenuation measurements, i.e., projection data, from the detector array is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

With known CT systems, projection data is collected from a helical or axial scan to generate sequential frames of images of an area, or organ, within a patient. A frame corresponds to a two dimensional slice taken through the imaged object, e.g., the patient. Typically, an operator attempts to minimize the amount of time required to generate each image by increasing the frame rate while minimizing image degradation.

At least one known CT system collects data utilizing a large flat panel digital x-ray device, or detector, having a plurality of pixels arranged in rows and columns. Each pixel includes a photosensor, such as a photodiode, that is coupled via a switching transistor to two separate address lines, a scan line and a data line. During operation, x-ray beams passing through the object are incident on the imaging device. The radiation incident on a scintillator material and the pixel photosensors measure, by way of change in the charge across the diode, the amount of light generated by x-ray interaction with the scintillator. As a result, each pixel produces a digital electrical signal that represents the intensity of an impinging x-ray beam.

To detect coronary calcification in a patient, images of the patient's heart are generated and reviewed to identify calcium deposits. This can be accomplished by detecting the average calcium concentration in a set of CT images. However, as a result of the data collection rate and the movement of the heart and the blood, the heart images may be blurred. On the other hand, the fluoroscopy mode of the digital x-ray device is capable of generating 30 frames per second or higher image rate which is sufficient to overcome blurring due to heart motion. However, the images may be difficult to view as a result of the structures which overlap over the heart. For example, the images may include ribs, a lung, and other surrounding soft tissue. These overlapping structures cause difficulty in identifying areas of calcium deposits.

To reduce the blurring of the images, it is desirable to provide an imaging system which gathers data at sufficiently high rate so that the heart motion is minimized. It would also be desirable to provide such a system which removes the overlapping structures from the images to improve the quality of the heart images.

BRIEF SUMMARY OF THE INVENTION

These and other objects may be attained in a digital x-ray imaging system which, in one embodiment, includes an reconstruction algorithm which filters collected data to remove overlapping, or stationary, structures so that clear enhanced images of a heart are generated. The enhanced images are then used to identify cardiac calcification in the heart. More particularly, and in accordance with one embodiment of the present invention, the imaging system includes an x-ray source and a flat panel digital detector array for high speed collection of projection data.

In one embodiment, after collecting a sequence of projection data, an estimated background is determined. More specifically, the estimated background is determined by generating an average of the entire sequence of data. The average represents the structures remaining stationary during data collection and an averaged or blurred heart. The stationary structures are then filtered, or removed, from the projection data by subtracting the estimated background from the projection data.

In another embodiment, difference data is determined between a selected frame of projection data and the remaining frames of projection data. An average difference value is then determined, for the entire image, or a specific region of interest. In one embodiment, by monitoring the average difference, the phase of the heart may be determined. More specifically, where the average difference represents the cardiac cycle of the heart, data collected from an opposite phase of the heart may be excluded from the collected data to improve image quality. Particularly, a maximum difference value may be utilized to exclude or assign a lower weight to the projection data collected during an opposite phase of the heart.

In another embodiment, an ECG signal representative of the phase of the heart is utilized to identify data collected when the heart is significantly out of phase with a reference frame of data. As discussed above, the data collected during these out of phase periods are then either excluded or lower weighted.

In yet another embodiment, the imaging system includes multiple x-ray sources and multiple detector arrays. By positioning these sources and detectors at different orientations, or angles, around a patient and time synchronizing the data, differential images are generated which provide depth information to further localize calcification.

By collecting and filtering the projection data sets as described above, identification of cardiac calcification level in the heart may be achieved. Particularly, by removing the overlapping structures and generating images of the moving heart, the quantity and location of the calcification within the heart may be identified.

DETAILED DESCRIPTION OF THE INVENTION

Figure 1:
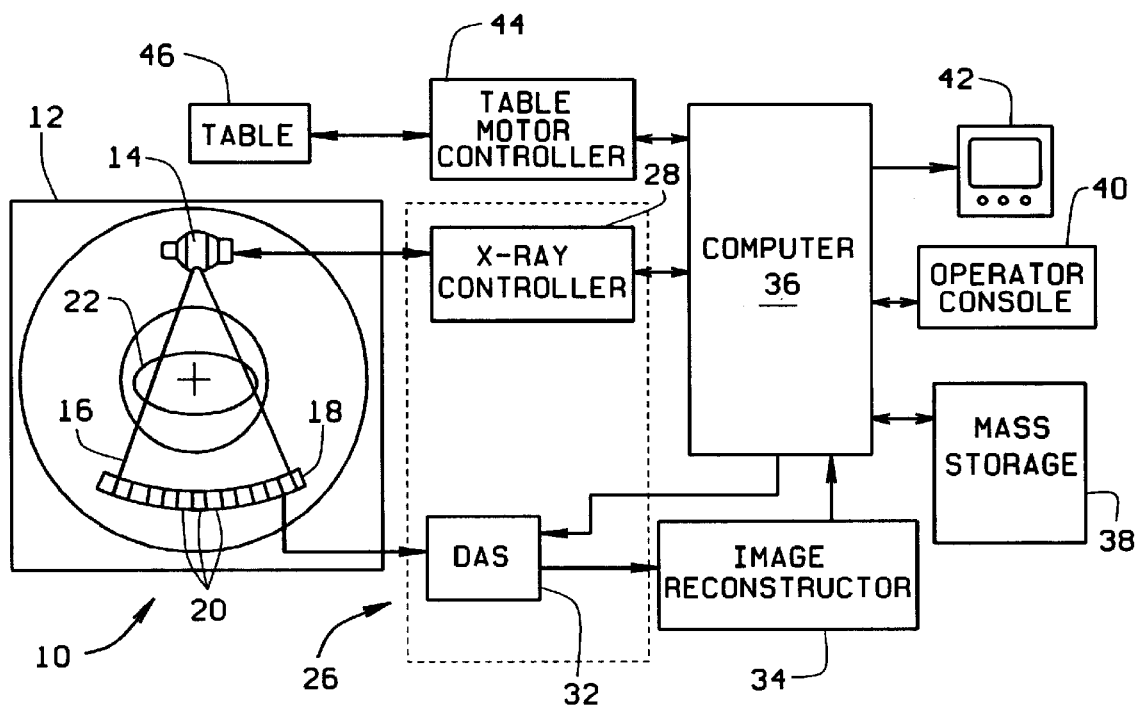
FIG. 1 is a block schematic diagram of an imaging system.

Referring to FIG. 1 and in an exemplary embodiment, an imaging system 10 generates images for performing cardiac diagnosis of a patient's heart (not shown). System 10 includes at least one x-ray source and at least one detector array for collecting projection data. Specifically and in one embodiment, system 10 includes an x-ray source 14 that projects a beam of x-rays 16 toward a digital detector array 18. In one embodiment, detector array 18 is fabricated in a panel configuration having a plurality of pixels (not shown) arranged in rows and columns so that an image is generated for an entire organ within patient 22, i.e., a heart (not shown). More specifically, the large flat panel digital x-ray includes a plurality of pixels arranged in rows and columns. Each pixel includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel produces a digital electrical signal that represents the intensity, after attenuation of patient 22, of an impinging x-ray beam 16. In various embodiment, detector array 18 is approximately 40 cm wide (x-axis) by 20 to 40 cm in height (z-axis) and is configured to produce projection data at a rate of up to 40 frames per second. Of course, in other embodiments, the size of detector array altered for the specific system requirements.

The operation of x-ray source 14 is governed by a control mechanism 26 of imaging system 10. Control mechanism 26 includes an x-ray controller 28 that provides power and timing signals to x-ray source 14. A data acquisition system (DAS) 32 in control mechanism 26 samples digital data from detector elements 20 for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32 and x-ray controller 28. In one embodiment, computer 36 operates a table motor controller 44 which controls a motorized table 46 to position patient 22. Particularly, table 46 moves portions of patient 22 within path of x-ray beam 16.

A reconstruction algorithm described below may be implemented in computer 36 using data collected from detector array 18. It will be apparent to those skilled in the art, of course, that such algorithm could be practiced in other components. For example, the algorithm may be practiced directly in image reconstructor 34 so that filtered data is supplied to computer 36. In addition, the algorithm is described as being performed on the original data for quality and computational simplicity. Of course, filtering could be performed in image space.

In one embodiment, the reconstruction algorithm is used to filter projection data to generate images for performing cardiac diagnosis of patient 22. Specifically, projection data rapidly collected using detector 18 are filtered, or corrected, to remove stationary objects, or structures, i.e., objects which overlap or overlay. Using the filtered projection data, which represents only the motion of the heart of patient 22, at least one enhanced image of the object is generated. The enhanced image is then used to identify cardiac calcification in the heart.

More specifically, a sequence of projection data is collected using detector array 18. The projection data includes a plurality of frames of reference data, i.e., at least a first frame and a second frame of projection data collected during several cycles of the heart. In one embodiment, the stationary position of detector 18 is adjusted so that detector 18 generates sequential frames of projection data for a selected area, or organ, of patient 22. After collecting the projection data, an estimated background of the entire sequence of projection data is then determined. More specifically, the estimated background data is determined by generating an average of the frames of projection data. This average of the projection data represents the structures which are overlapping or stationary during data collection. In addition, as a result of the data being collected during several cardiac cycles, the average of the projection data represents an averaged or blurred heart. As a result, the average of the frames of projection data is a good representation of the background to be removed.

More specifically, each frame of projection data include a plurality of pixel locations with each location having a pixel intensity. In one embodiment, the estimated background is determined by determining an average pixel intensity for each respective pixel location of the projection data. More specifically, the average pixel intensity is determined by summing the intensity for each respective pixel location of each frame of the projection data. Particularly, and in one embodiment, the average pixel intensity for a certain pixel location of the projection data is determined in accordance with:

$$\text{Average Intensity of Pixel}(i, j) = \frac{\sum_{k=1}^{N} S_k(i, j)}{N}.$$

where:

$N = $ a number of frames of projection data, and $S_k(i, j) = $ intensity of pixel $(i, j)$ of the $k_{th}$ frame of projection data.

The estimated background is then determined, or generated, utilizing the average intensity of each pixel.

Filtered image data representing the removal of the overlapping structures is then generated by subtracting the estimated background from each frame of projection data. More specifically, frames of filtered data are generated by subtracting the average projection data from each frame of collected projection data. The filtered image data is then processed in accordance with methods known in the art to generate an image of the heart with the overlapping structures removed. In one embodiment, the enhanced image may be generated using a known filtered backprojection method and displayed on display 42.

In another embodiment, a selected portion of the collected projection data is excluded or weighted differently in determining the estimated background to reduce the imprint of the heart that is not related to the background of the current heart cycle. More specifically, utilizing the entire sequence of reference data as described above, the estimated background includes data reflecting the heart during several cardiac cycles. As a result of including these different cycles, the estimated background includes information not related to the background of the current heart reference frame data. To overcome this difficulty, difference data is generated by determining a difference between a selected frame of projection data and all other frames of projection data, i.e., non-selected frames. More specifically, after determining a difference between data for a selected reference frame and each of remaining frame of projection data, an average difference is determined for the entire sequence of projection data. In another embodiment, the average difference is determined for a specific region of interest.

Figure 2:
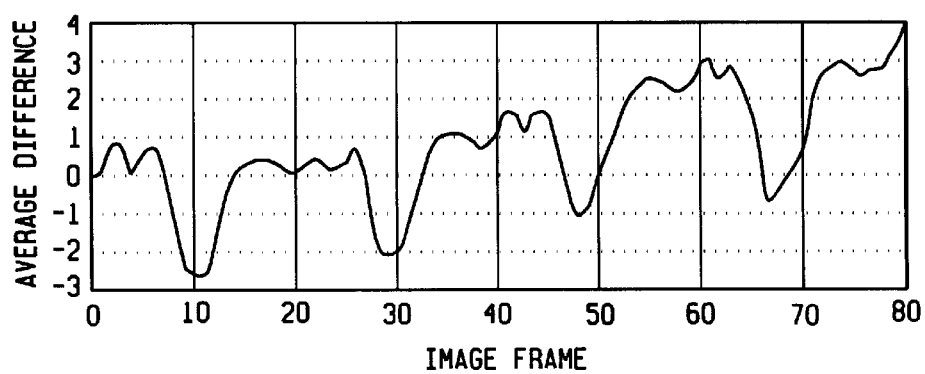
FIG. 2 is a graph of an average difference error.

For example, as shown in FIG. 2, the average difference is zero for a comparison of a first frame to a first frame and gradually increases for comparison of adjacent frames, i.e, a comparison of a first and second frame, a comparison of a first and third frame, etc. A maximum difference is achieved when the heart is in an opposite phase in a cardiac cycle. For example, if the reference frame is obtained in a systolic phase, the maximum difference is generated when compared to a frame obtained during a diastolic phase. The average error will gradually decrease as the heart returns to the same cardiac phase as the reference frame. Therefore, the average error is a good representation of the cardiac cycle. More specifically and as shown in FIG. 2, the valleys in the graph represent the condition where the phase of the heart is significantly different from that of the reference frame. The general upward drift in the difference is a result of the heart never exactly duplicating its shape and location from cycle to cycle.

Utilizing the average difference, selected frames of projection data, i.e, those which are significantly out of phase with the reference frame, may be identified. For example, utilizing known algorithms such as various correlation or wavelet approaches, the valleys of the average difference may be identified to select, or identify, the out of phase portions of the projection data. The out of phase projection data are then identified as a selected portion of the projection data and the remaining projection data is identified as a non-selected portion. After identifying the out of phase frame data, the selected portion of the projection data may be excluded from the estimated background determination as described above. In an alternative embodiment, the identified frames are assigned lower weights during a weighted backprojection process as known in the art. More specifically, frames in the selected portion of the projection data are assigned a first weight and the frames in the non-selected data are assigned a second weight. In one embodiment, the second weight is greater than the first weight. For example, the second weight equals one and the first weight is 0.2.

In another embodiment, rather than using the average difference, the algorithm utilizes an ECG signal to identify those frames which are significantly out of phase with the reference frame. More specifically, the ECG signal is utilized to identify when the heart is significantly out of phase with the reference frame. As described above, those frames significantly out of phase may then be excluded or assigned a lower weight.

Alternatively, the weight is selected to be proportioned or a function of the heart "phase". When the frame is in-phase with the reference, for example, when the phase of the heart in the frame and the reference are approximately equal as determined by the ECG signal, the weight equals one. When the heart in the frame and the reference are in an opposite phase, the weight equals zero. In one embodiment, between in-phase and an opposite phase, the weight varies continuously as a function of the "phase".

Figure 3:
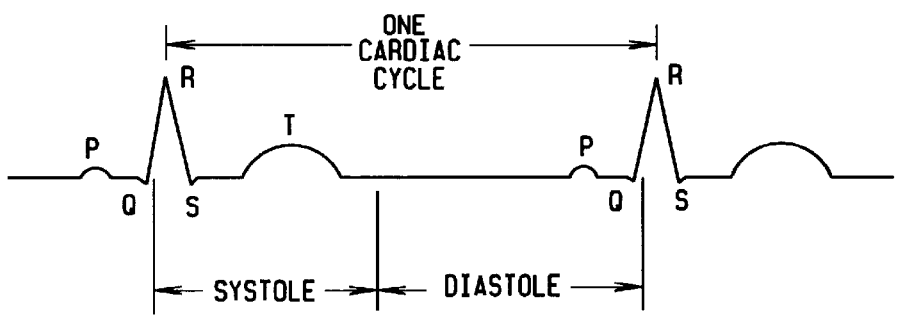
FIG. 3 is an ECG signal waveform.

For example and in one embodiment, the ECG signal, representative of a cardiac cycle of the heart, is generated by an ECG subsystem (not shown), as known in the art, and is coupled to system 10, i.e., computer 36. As shown in FIG. 3, the ECG signal waveform illustrates one cardiac cycle including a systole condition, or period, and a diastole condition, or period of the heart. The portion of the ECG signal which is labeled Q, R and S is referred to as the QRS complex, in which the R-feature, or R-wave, is the most prominent, highest amplitude, feature of the entire ECG signal. The cardiac cycle is typically defined as beginning with a R-wave and continuing until the occurrence of the next R-wave.

Using the ECG signal, the selected out of phase portions of the projection data may be identified. In one embodiment, depending on the speed of system 10, a determined number of frames of projection data may be collected during each cardiac cycle. Utilizing the ECG signal, those selected portions of the projection data may be excluded from the estimated background as described above. For example, where forty frames of projection data are collected during four cycles of the heart, an estimated background of the first cycle is generated by excluding the portion of the projection data representing cycles two through four. More specifically, using the ECG signal, the estimated background is determined by utilizing frames one through ten and by excluding frames eleven through forty. Similarly, the estimated background for the second cycle may be determined utilizing frames 11 through 20 and excluding frames 1 through 10 and 21 through 40. The same process may be repeated in a similar manner for the third and fourth cycles.

In a similar fashion, filtered data for the first cycle may be generated from the second frame of data. The estimated background data for the first cycle uses frames 1 to 10. A similar operation may be performed by selecting a third, fourth, or any projection frame for the filtered data. Once the estimated background is subtracted from the corresponding frame data, a set of enhanced images may be obtained. These enhanced images may be displayed in a cine mode to depict the cardiac motion.

In addition to the motion of the heart, the projection data may include a position change, or movement, caused by a small amount of motion by patient 22. This motion causes the projection data to appear as though stationary objects have moved or changed position. To correct for this motion, prior to filtering, the frames of the projection data are aligned, or corrected. More specifically, by performing a frame to frame registration of the data, the projection data is aligned so that the stationary objects are located in the same location. More specifically and in one embodiment, using known techniques, each frame is aligned so that the stationary structures within patient 22 are located in the same geographical position in each frame.

For example, where patient 22 exhales between collection of the first and second frame of projection data, the second frame reflects data from an area geographically shifted from the first frame. To correct for this movement, a frame to frame registration of the frame data is utilized to align the first and second frames so that each frame represents the same area of patient 22.

Figure 4:
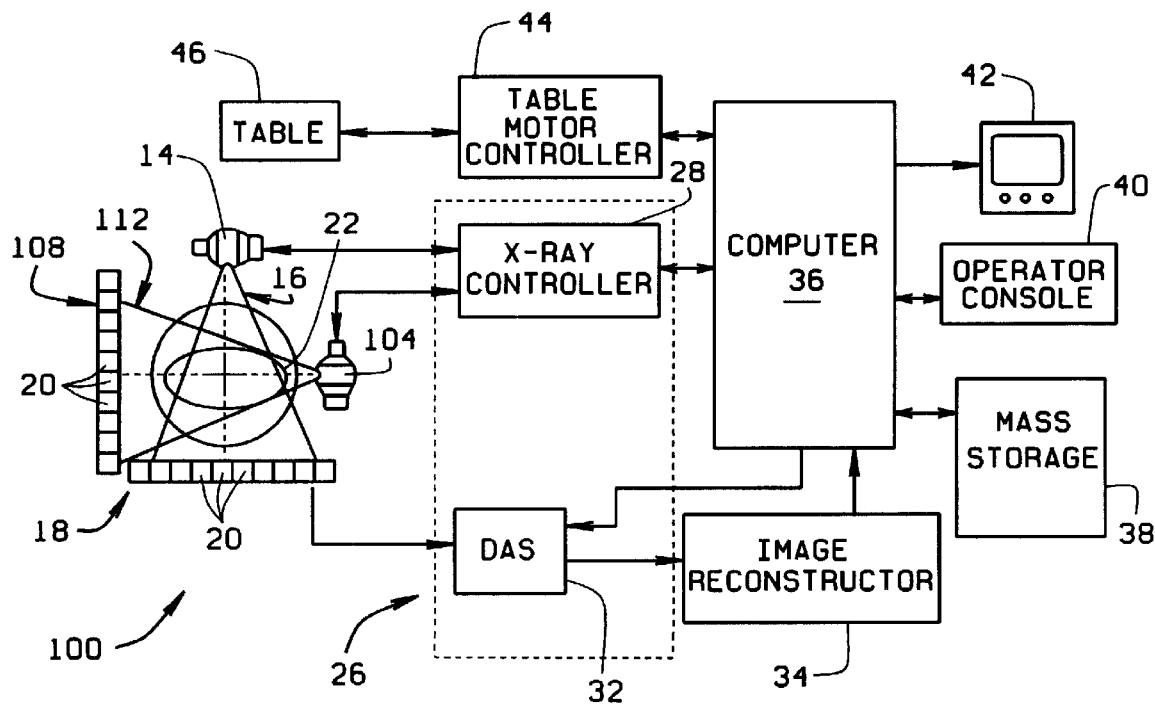
FIG. 4 is another embodiment of the imaging system in FIG. 1.

FIG. 4 is a simplified schematic view of another embodiment of an imaging system 100 in accordance with the present invention. Components in system 100 which are identical to components in system 10 (FIG. 1) are identified in FIG. 3 using the same reference numerals as used in FIG. 1. In one embodiment, imaging system 100 includes a first x-ray source 14, a second x-ray source 104, which is similar to source 14, a first detector array 18, and a second detector array 108, which is similar to detector 18. First source 14 and first detector array 18 are aligned so that a first x-ray beam 16 is radiated from source 14 toward detector 18 along a first angle. Second source 104 and second detector 108 are aligned so that a second x-ray beam 112 is radiated from source 104 toward detector 108 along a second angle. More specifically and in one embodiment where patient 22 is positioned on table 46, x-ray source 14 and detector array 18 are positioned so that x-ray beam 16 is radiated along a first angle relative to patient 22. Source 104 and detector 108 are positioned so that an x-ray beam 112 is radiated along a second angle with respect to patient 22. During each cardiac cycle, projection data is collected using detector 18 and detector 108 to generate images of the patient's heart. Of course, the respective angles of source 14 and detector 18 and source 104 and detector 108 may be altered to any desired angle relative to each other and patient 22.

As a result of the projection data being collected by detector 18 at a different point in time than the projection data collected by second detector 108, in one embodiment, the algorithm synchronizes the respective projection data so that the projection data are aligned in time. For example and as shown in FIG. 3, x-ray source 14 and detector array 18 are positioned so that x-ray beam 16 radiated from source 14 in an x-axis direction with respect to patient 22 lying on table 46. Source 104 and detector 108 are positioned so that an x-ray beam 112 is radiated in a y-axis direction with respect to patient 22. After collecting the projection data sets using detector 18 and detector 108, the projection data sets are aligned, or adjusted to reflect the same point in time during a cardiac cycle of the patient's heart, e.g., 0.5 seconds after a R-wave of the heart.

Utilizing the synchronized projection data collected from at least two different angles, depth information images are generated to further localize the calcification. More specifically, where the first angle is not equal to the second angle, the synchronized images may be utilized to determine a specific location of the calcification. Particularly, using known tomographic reconstruction algorithms, the synchronized projection data collected from at least two angles may be used to generate the depth information images.

The above described system collects and filters the projection data sets to identify cardiac calcification in the heart. Particularly, by using high speed data collection to generate images of the moving heart and removing the overlapping structures, the quantity and location of the calcification within the heart may be identified.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for generating an image of an object using an imaging system, the object having stationary structures and at least one moving structure, the imaging system including at least one x-ray source and at least one x-ray detector array, said method comprising the steps of:

collecting projection data using each detector array;

determining an average difference of the projection data; and filtering the projection data to remove the stationary objects using the determined average difference of the projection data.

2. A method in accordance with claim 1 further comprising the step of generating at least one enhanced image of the object using the filtered projection data.

3. A method in accordance with claim 2 wherein filtering the projection data to remove the stationary objects comprises the steps of:

utilizing the determined average difference of projection data to generate estimated background data; and subtracting the estimated background data from the projection data.

4. A method in accordance with claim 3 wherein subtracting the estimated background data from the projection data comprises the step of subtracting average data from each frame of projection data.

5. A method in accordance with claim 3 wherein each frame of projection data includes a plurality of pixels, and wherein generating estimated background data comprises the step of:

determining an average intensity of each pixel in accordance with:

$$\text{Average Intensity of Pixel}(i, j) = \frac{\sum_{k=1}^{N} S_k(i, j)}{N}.$$

where:

$N$ = a number of frames of projection data, and $S_k(i, j)$ = intensity of pixel $(i, j)$ of the $k_{th}$ frame of projection data.

6. A method in accordance with claim 1 wherein collecting projection data comprises the step of collecting at least two frames of projection data.

7. A method in accordance with claim 6 wherein determining an average difference of the projection data comprises the steps of:

determining difference data between a first frame of projection data and at least a second frame of projection data; and determining a difference data average.

8. A method in accordance with claim 7 wherein filtering the projection data to remove the stationary objects comprises the step of identifying a selected portion of projection frames using the difference data average.

9. A method in accordance with claim 8 further comprising the steps of:

removing the selected portion of projection frames from the projection data to generate filtered projection data; and generating an image of the object using the filtered projection data.

10. A method in accordance with claim 8 further comprising the steps of:
   assigning a first weight to the selected portion of projection frames;
   assigning a second weight to non-selected portion of projection frames; and
   generating an image of the object using the using the weighted projection frames.

11. A method in accordance with claim 10 further comprising the step of identifying a motion phase of the moving structure.

12. A method in accordance with claim 11 wherein the first weight and the second weight are each a function of the motion phase of the moving structure.

13. A method in accordance with claim 6 wherein the system further includes an ECG signal representative of a cardiac cycle of the heart, and wherein filtering the projection data to remove the stationary objects comprises the step of identifying a selected portion of projection frames using the ECG signal.

14. A method for generating an image of an object using an imaging system including a first x-ray source, a first detector array, a second x-ray source, and a second detector array comprises the steps of:
   collecting at least two frames of first projection data using the first detector array wherein the first x-ray source and first detector array aligned along a first angle relative to the object;
   collecting at least two frames of second projection data using the second detector array, wherein the second x-ray source and the second detector array aligned along a second angle relative to the object;
   determining an average difference of the at least two frames of first projection data;
   determining an average difference of the at least two frames of second projection data; and
   filtering the first projection data and the second projection data to remove the stationary objects using the respective determined average differences of the first projection data and the second projection data.

15. A method in accordance with claim 14 wherein the first angle is not equal to the second angle, and wherein said method further comprises the step of synchronizing the first projection data and the second projection data.

16. A method in accordance with claim 14 further comprising the step of performing a frame to frame registration of each respective frame of the first projection data and the second projection data.

17. An imaging system for generating an image of an object, the object having stationary structures and at least one moving structure, said imaging system including at least one x-ray source and at least one x-ray detector array and configured to:
   collect projection data using each said detector array;
   determine an average difference of the projection data; and
   filter the projection data to remove the stationary objects using the determined average difference of the projection data.

18. An imaging system in accordance with claim 17 further configured to generate at least one enhanced image of the object using the filtered projection data.

19. An imaging system in accordance with claim 18 wherein to filter the projection data to remove the stationary objects, said system configured to:
   utilize said determined average difference of projection data to generate estimated background data; and
   subtract the estimated background data from the projection data.

20. An imaging system in accordance with claim 19 wherein to subtract the estimated background data from the projection data, said system configured to subtract the average data from each frame of projection data.

21. An imaging system in accordance with claim 19 wherein each frame of projection data includes a plurality of pixels, and wherein to generate estimated background data using the projection data, said system configured to determine an average intensity of each pixel in accordance with:

$$\text{Average Intensity of Pixel}(i, j) = \frac{\sum_{k=1}^{N} S_k(i, j)}{N}.$$

where:
$N$ = a number of frames of projection data, and
$S_k(i, j)$ = intensity of pixel $(i, j)$ of the $k_{th}$ frame of projection data.

22. An imaging system in accordance with claim 17 wherein to collect projection data, said system configured to collect at least two frames of projection data.

23. An imaging system in accordance with claim 22 wherein to determine an average difference of the projection data, said system configured to:
   determine difference data between a first frame of projection data and at least a second frame of projection data; and
   determine a difference data average.

24. An imaging system in accordance with claim 23 wherein to filter the projection data to remove the stationary objects, said system configured to
   identify a selected portion of projection frames using the difference data average.

25. An imaging system in accordance with claim 24 further configured to:
   remove the selected portion of projection frames from the projection data to generate filtered projection data; and
   generate an image of the object using the filtered projection data.

26. An imaging system in accordance with claim 24 further configured to:
   assign a first weight to the selected portion of projection frames;
   assign a second weight to non-selected portion of projection frames; and
   generate an image of the object using the using the weighted projection frames.

27. An imaging system in accordance with claim 26 further configured to identify a motion phase of the moving structure.

28. An imaging system in accordance with claim 27 wherein said first weight and said second weight are each a function of said motion phase of the moving structure.

29. An imaging system in accordance with claim 22 wherein said system further includes an ECG signal representative of a cardiac cycle of the heart, and wherein to filter the projection data to remove the stationary objects, said system configured to identify a selected portion of projection frames using said ECG signal.

30. An imaging system for generating an image of an object, the object having stationary structures and at least one moving structure, said imaging system comprising a first x-ray source, a first detector array, a second x-ray source, and a second detector array, said system configured to:

collect at least two frames of first projection data using said first detector array wherein said first x-ray source and said first detector array aligned along a first angle relative to the object;

collect at least two frames of second projection data using said second detector array, wherein said second x-ray source and said second detector array aligned along a second angle relative to the object;

determine an average difference of said at least two frames of first projection data;

determine an average difference of said at least two frames of second projection data; and filter said first projection data and said second projection data to remove the stationary objects using the respective said determined average differences of said first projection data said second projection data.

31. An imaging system in accordance with claim 30 wherein said first angle is not equal to said second angle, and wherein said system further configured to synchronize the first projection data and the second projection data.

\* \* \* \* \*

UNITED STATES PATENT AND TRADEMARK OFFICE
CERTIFICATE OF CORRECTION

PATENT NO. : 6,226,350 B1
DATED : May 1, 2001
INVENTOR(S) : Jiang Hsieh

Page 1 of 1

It is certified that error appears in the above-identified patent and that said Letters Patent is hereby corrected as shown below:

Column 10,
Line 54, delete the duplicate wording "using the".

Signed and Sealed this

Fifth Day of March, 2002

Attest:

JAMES E. ROGAN
Attesting Officer  Director of the United States Patent and Trademark Office